United States Patent [19]
Lanza

[11] Patent Number: 5,930,314
[45] Date of Patent: Jul. 27, 1999

[54] CODED APERTURE IMAGING

[75] Inventor: Richard C. Lanza, Brookline, Mass.

[73] Assignee: Massachusetts Institute of Technology, Cambridge, Mass.

[21] Appl. No.: 08/866,717

[22] Filed: May 30, 1997

Related U.S. Application Data

[60] Provisional application No. 60/018,858, May 31, 1996, and provisional application No. 60/034,956, Jan. 15, 1997.

[51] Int. Cl.$^6$ .................................. G21G 1/06; G01T 1/00
[52] U.S. Cl. ................. 376/159; 250/358.1; 250/363.06; 250/390.04
[58] Field of Search ........................... 376/159, 161–166; 250/358.1, 359.1, 360.1, 363.06, 390.01, 390.04, 390.07; 382/281; 378/2, 149

[56] References Cited

U.S. PATENT DOCUMENTS

| | | | |
|---|---|---|---|
| 3,748,470 | 7/1973 | Barrett | 250/363.06 |
| 3,997,787 | 12/1976 | Fearon et al. | 250/359 |
| 4,017,730 | 4/1977 | Barrett | 250/363.06 |
| 4,126,783 | 11/1978 | Lanza | 250/363.02 |
| 4,209,780 | 6/1980 | Fenimore et al. | 250/363.06 |
| 4,435,838 | 3/1984 | Gourlay | 250/363.06 |
| 4,514,632 | 4/1985 | Barrett | 250/363.06 |
| 4,864,142 | 9/1989 | Gomberg | 250/390.04 |
| 5,006,299 | 4/1991 | Gozani et al. | 376/159 |
| 5,078,952 | 1/1992 | Gozani et al. | 376/159 |
| 5,098,640 | 3/1992 | Gozani et al. | 376/166 |
| 5,114,662 | 5/1992 | Gonzani et al. | 376/159 |
| 5,606,165 | 2/1997 | Chiou et al. | 250/363.06 |

FOREIGN PATENT DOCUMENTS

| | | |
|---|---|---|
| 0 061 547 | 10/1992 | European Pat. Off. . |
| 2 606 160 | 5/1988 | France . |
| 2 274 708 | 8/1994 | United Kingdom . |
| WO 8803275 | 5/1988 | WIPO . |

OTHER PUBLICATIONS

Schaich, P.C. et al., "Automatic Image Analysis for Detecting and Quantifying Gamma–Ray Sources in Coded–Aperture Images", *IEEE Transactions on Nuclear Science*, vol. 43, No. 4 (Aug. 1996) pp. 2419–2426.

(List continued on next page.)

*Primary Examiner*—Daniel D. Wasil
*Attorney, Agent, or Firm*—Thomas J. Engellenner; C. Eric Schulman

[57] ABSTRACT

This invention provides coded aperture imaging apparatus and methods for the detection and imaging of radiation which results from nuclear interrogation of a target object. The apparatus includes: 1) a radiation detector for detecting at least a portion of the radiation emitted by the object in response to nuclear excitation and for producing detection signals responsive to the radiation; 2) a coded aperture disposed between the detector and the object such that emitted radiation is detected by the detector after passage through the coded aperture; and 3) a data processor for characterizing the object based upon the detection signals from the detector and upon the configuration of the coded aperture. The method includes the steps of: 1) disposing a coded aperture in selected proximity to the object; 2) bombarding the object with a interrogation beam from a source of excitation energy; 3) detecting, with a detector, at least a portion of the radiation emitted in response to the interrogation beam, the detector producing detection signals responsive to the radiation, the detector being disposed so that the coded aperture is between the detector and the object and such that emitted radiation is detected by the detector after passage through the coded aperture; and 4) processing the detection signals to characterize the object based upon radiation detected by the detector after passage through the coded aperture, and based upon the configuration of the coded aperture.

9 Claims, 9 Drawing Sheets

OTHER PUBLICATIONS

Fink, C.L., et al., "Evaluation of Neutron Techniques for Illicit Substance Detection", *Nuclear Instruments & Methods in Physics Research*, B 99 (1995) pp. 748–752.

Byard, K., Ramsden, D., "Coded Aperture Imaging Using Imperfect Detector Systems", *Nucl. Instr. and Meth. in Phys. Res.* A 342 (1994) pp. 600–608.

Bell, C.J. et al., "Analysis of Complex Targets Using Fast Neutrons", *SPIE Vol. 2092 Substance Detection Systems* (1993) pp. 514–524.

Rowe, R.K. et al., "A Stationary Hemispherical SPECT Imager for Three–Dimensional Brain Imaging", *The Journal of Nuclear Medicine*, vol. 34, No. 3 (Mar. 1993) pp. 474–480.

In 't Zand, J.J.M., "Coded Aperture Camera Imaging Concept", an excerpt from Ph.D. Thesis, University of Utrecht (1992) Web Page: http://lheawww.gsfc.nasa.gov/docs/cai/coded_intr.html).

Ziock, K.P. et al., "A Gamma–Ray Imager for Arms Control", *IEEE Transactions on Nuclear Science*, vol. 39, No. 4 (1992) pp. 1046–1050.

Fenimore, E.E., "Time–Resolved and Energy–Resolved Coded Aperture Images with URA tagging", *Applied Optics*, vol. 26, No. 14 (Jul. 15, 1987) pp. 2760–2769.

Chou, Chien et al., "Quantum Noise of Fourier–Coded Aperture Imaging System", *Jpn. J. Appl. Phys.* vol. 33 (1994) pp. 2072–2078.

Roques, J.P., "Fast Decoding Algorithm for Uniformly Redundant Arrays", *Applied Optics*, vol. 26, No. 18 (Sep. 15, 1987) pp. 3862–3865.

Smith et al., "Image Reconstruction from Coded Data: I. Reconstruction Algorithms and Experimental Results", *J. Opt. Soc. Am. A*, vol. 2, No. 4 (Apr. 1985) pp. 491–500.

Paxman et al., "Image Reconstruction from Coded Data: II. Code Design", *J. Opt. Soc. Am. A.*, vol. 2, No. 4 (Apr. 1985) pp. 501–509.

Skinner, G.K. "Imaging with Coded–Aperture Masks", *Nuclear Instruments and Methods in Physics Research*, vol. 221 (1984) pp. 33–40.

Simpson, R.G. and Barrett, H.H., "Coded–Aperture Imaging", *Imaging for Medicine*, vol. 1, Chapter 8, pp. 217–311 (Plenum Press, New York, 1980).

Fenimore, E.E. et al., "Uniformly Redundant Arrays: Digital Reconstruction Methods", *Applied Optics*, vol. 20, No. 10 (May 15, 1981) pp. 1858–1864.

Fenimore, E.E., "Coded Aperture Imaging: The Modulation Transfer Function for Uniformly Redundant Arrays", *Applied Optics*, vol. 19, No. 14 (Jul. 15, 1980) pp. 2465–2471.

Proctor, R.J. et al., "The Design of Optimum Coded Mask X–ray Telescopes", Mon. Not. R. astr. Soc. vol. 187 (1979) pp. 633–643.

Gunson et al., "Optimum Design of a Coded Mask X–Ray Telescope for Pocket Applications", Mon. Not. R. astr. Soc. vol. 177 (1976) pp. 485–497.

Fenimore, E.E., "Coded Aperture Imaging: Predicted Performance of Uniformly Redundant Arrays", *Applied Optics*, vol. 17, No. 22 (Nov. 15, 1978) pp. 3562–3570.

Fenimore, E.E., et al., "Coded Aperture Imaging with Uniformly Redundant Arrays", *Applied Optics*, vol. 17, No. 3 (Feb. 1, 1978) pp. 337–347.

CODED APERTURE IMAGING

CROSS REFERENCES

The present application claims the benefit of, and incorporates by reference, the commonly owned, co-pending U.S. provisional application No. 60/018,858 filed May 31, 1996 and the commonly owned, co-pending U.S. provisional application No. 60/034,956 filed Jan. 15, 1997.

Government Rights

The U.S. Government has rights in this invention pursuant to Federal Aviation Administration Grant No. 93-G-053.

BACKGROUND OF THE INVENTION

The technical field of this invention is elemental detection and imaging and, in particular, methods and apparatus for the detection of the elemental composition of objects by nuclear interaction analysis. The invention is useful in the detection of contraband concealed within cargo containers, suitcases, parcels or other objects. As used herein, the term "contraband" includes, but is not limited to, explosives, drugs, and alcohol.

During the past ten years, the Federal Aviation Administration (FAA) of the US Department of Transportation has funded considerable research into the prevention of illegal transportation of explosives and drugs. One goal of this research is to create a detection system for airports that will screen passengers' luggage for explosives, as well as other contraband. Once this system is implemented, it is likely to be applied to other inspectional purposes, such as the screening of cargo containers at custom stations, ports, etc., as well.

The probability of the existence of explosives in a piece of luggage at an airport is approximately 1 in 10 million. To avoid lengthy delays at airport security check points, a practical contraband detection system at an airport requires a high detection speed, e.g. 6–8 seconds per piece of luggage and an acceptable false alarm rate. The false alarm rate can be defined as m/n, where n equals the number of the suitcases that the system determines to contain contraband, and m equals the number of suitcases that, upon inspection, do not in fact contain explosives. A false alarm rate of 10–20% or less is preferable.

Similar processing constraints apply to inspection of truck and rail cargo containers at border crossings and other security check points. In both applications, nondestructive detection is required. Damaging effects, such as the activation of the objects under examination, must be minimized. Furthermore, spatial resolution on the order of several centimeters in each dimension is highly desirable.

Various techniques are known for detecting contraband. Metal detectors are routinely used in airports to screen carry-on luggage. While metal detectors are useful in detecting metal weapons they are not imaging systems and most often can not distinguish between weapons and other metallic objects. X-ray imaging systems provide a rudimentary view of objects within a suitcase or container, but suffer from a general inability to image low atomic weight objects (e.g., plastic weapons, explosives and drugs). Moreover, images from conventional X-ray detectors can be stymied by materials, such as metal foils or coatings, that absorb the relatively low energy X-ray radiation and thereby shield the contents from view. Further, X-ray systems determine density or average atomic number but not the existence of explosives, per se.

Ideally, a method of detecting contraband should be capable of distinguishing illegal materials from the typical objects found in luggage or cargo based on distinctive characteristics of the contraband. Thus, elemental analysis of the object undergoing inspection is an important goal for state-of-the-art inspection systems. Typically, explosives have a high nitrogen content, a low carbon-to-oxygen ratio, and high nitrogen and oxygen densities. Drugs, such as cocaine and heroin, have been shown to have high carbon-to-oxygen ratios, high carbon and chlorine contents, and little nitrogen.

Included within nuclear interaction analysis are nuclear emission detection techniques. Nuclear emission detection techniques are based on the realization that characteristic elemental composition data can be obtained from the induced emission of radiation, e.g. gamma-rays, or particles, from the nuclei of the atoms of an object undergoing inspection. According to these techniques a source of radiation, e.g. a particle beam, such as a neutron beam, or a source of hard X-rays or gamma rays, bombards an object under investigation, triggering the nuclei of the object to emit characteristic radiation. In these techniques, referred to generally as "nuclear emission" analyses, different contraband molecules are identified based on their unique nuclear emissions in response to such high energy interrogation. The related term nuclear fluorescence is most commonly used to describe the emission of X-ray radiation by nuclei in response to excitation by X-rays. However, for the purposes of this application nuclear fluorescence will indicate the emission of photons by nuclei in response to excitation by radiation (electromagnetic or particulate).

The emissions are analyzed for characteristic energy profiles that indicate the elemental structures present in the object. Advantageously, nuclear methods can detect the general properties of contraband by identifying and localizing (imaging) the chemical constituents of an object under investigation.

One technique of particular interest at present is known as "fast neutron" analysis. In this approach, fast neutrons (e.g., having energies greater than about 1 MeV, preferably greater than a few MeV) are generated and used to interrogate the object undergoing inspection. The neutrons strike the nuclei of the object and induce gamma ray emissions. Fast neutrons are used because they have high penetration capability and large activation cross-sections with elements of interest, e.g. carbon, nitrogen, and oxygen.

Simple neutron spectroscopy systems merely analyze the spectrum of radiation induced by fast neutrons to detect characteristic emissions. Unfortunately, such data are often insufficient for detection of contraband when the volume of the object is large because the telltale signatures of contraband will be scrambled with the emissions from all the other contents of the object.

Considerable research has been directed towards the development of position-sensitive detection systems for fast neutron and other nuclear emission analyses. Radiographic techniques can be used to construct images. By employing a two-dimensional array of detectors (or a scanning one-dimensional array) a two-dimensional distribution of neutron interaction cross-sections of the object under examination can be obtained. For greater spatial resolution, tomographic approaches can be employed (e.g., using multiple projections from orthogonal arrays of detectors) to construct a three-dimensional image of the emissions. In another approach to acquiring three dimensional data, pulsed neutron beams have been proposed for use with detector arrays, whereby the timing of the detected emissions can provide a degree of depth resolution.

All of the known techniques for nuclear emission detection suffer from one or more deficiencies which make them unattractive for large scale implementation. The spatial resolution of such systems is often compromised by the need to minimize the dose to each object, the limited neutron source strength, and the desire to maintain rapid throughput of objects. Present techniques require strong sources of interrogating radiation. These sources are generally expensive and unreliable. With respect to the requirement of rapid throughput, multiple projection arrays and synchronous timing of such arrays (or pulsed neutron beams) add to the computational overhead and likewise limit throughput. Moreover scanning systems that require moving parts often introduce artifacts that degrade the spatial resolution of the system.

There exists a need for better methods and systems for remote inspection of objects, in general, and for detection of contraband in containers, in particular. A simplified remote inspection system that can provide practical spatial resolution while making efficient use of an interrogating radiation source would satisfy a long-felt need in the art.

SUMMARY OF THE INVENTION

Methods and apparatus for detection of the elemental composition of objects by nuclear interaction analysis are disclosed employing coded aperture detection systems. Coded aperture systems provide a simplified apparatus for rapid spatial resolution of radiation produced as a result of nuclear interrogation given a relatively weak source of interrogating radiation.

In one aspect of the invention, an apparatus is disclosed for analyzing radiation emitted by an object. The apparatus can include: 1) a radiation detector array for detecting at least a portion of the radiation emitted by the object in response to nuclear interrogation and for producing detection signals responsive to the radiation; 2) a coded aperture having a predetermined configuration disposed between the detector array and the object such that the emitted radiation is detected by the detector array after passage through the coded aperture; and 3) a data processor for characterizing the object based upon the detection signals from the detector array and based upon the predetermined configuration of the coded aperture.

This invention further provides a method of analyzing radiation emitted by an object in response to nuclear interrogation. The method includes the steps of: 1) disposing a coded aperture in selected proximity to the object; 2) interrogating the nuclei of the object with an energy source, the interrogation resulting in emitted radiation; 3) detecting at least a portion of the emitted radiation with a detector that produces detection signals responsive to the emitted radiation, the detector being disposed so that the coded aperture is situated between the detector and the object and such that emissions are detected by the detector after passage through the coded aperture; and 4) processing the detection signals to characterize the object based upon the detected emitted radiation and based upon the predetermined configuration of the coded aperture. In a preferred embodiment, the nuclei of the object under investigation are excited by neutron bombardment.

The systems and methods of the present invention are based on the discovery that coded apertures provide a simple mechanism for obtaining position-sensitive nuclear emission data from a two-dimensional array of detectors. Essentially, a coded aperture filters or encodes an image data set in a manner that allows decoding on a unit volume ("voxel") basis, i.e. a three dimensional (tomographic) reconstruction.

In one embodiment, the present invention employs a fast neutron beam to bombard the object under examination, and gamma rays emanate because of neutron capture or neutron inelastic scattering with the nuclei of the object. Neutron activation usually designates only a neutron capture (n,γ) reaction, in which a nucleus captures a neutron and emits a gamma ray. For the purposes of this application neutron activation describes any neutron-nucleus interaction that results in the nuclear emission of a gamma-ray. Neutron activation analysis is an analysis technique that quantitatively determines the nuclear elemental densities in the object under neutron bombardment based on the precise measurement of the neutron-induced gamma rays.

According to this embodiment, different gamma-ray energy spectra correspond to the nuclei of different nuclear elements in the object; thus, the emitted gamma rays that form the energy spectra are characteristic to the nuclear elements and are called signature gamma rays. By precisely measuring these gamma-ray spectra (energy versus intensity), it is possible to determine the elemental composition of the source. The signature gammaray intensity (i.e. the number of counts) is proportional to the multiplication of the neutron interaction cross-sections with the nuclear elemental density. Typically, only signature gamma rays of high energies (E>1 MeV) are considered. These gamma-rays emanate from the object under examination with very little attenuation.

By providing a coded aperture between the object under investigation and the detector array, the imaging system, according to one embodiment of the invention, can use a data processor to substantially correlate particular gamma-ray spectral information with a particular unit volume or voxel based on the predetermined configuration of the coded aperture. Importantly, the sterradian subtended by a coded aperture and an associated detector array is typically large compared to a single collimated detector. Thus, coded aperture systems are superior to collimated detectors in that they utilize a large portion of the radiation emitted by the target object, while concurrently providing image data. As a consequence, the cost of the required neutron source is reduced, and small sealed tube neutron sources developed and produced for the oil exploration industry can be used rather than large expensive accelerators. Thus, a relatively inexpensive and mobile unit can be produced for field use.

In sum, the invention improves the sensitivity of detection by a factor of as much as thirty as compared to previous techniques. Further, the increase in sensitivity is accomplished with improved spatial resolution.

The coded aperture detection methods of the present invention can take the form of a planar imaging technique and can operate with only one projection; accordingly the system is simple and the detection time is small because no mechanical rotations are involved. The methodology is similar to planar radiography, but the reconstructed images have depth information; thus this technique has tomographic capability.

The term "nuclear interrogation" is intended to encompass various techniques for interrogating the nuclei of an object undergoing inspection, including but not limited to techniques using high energy X-rays, gamma rays, neutrons and other high energy particles. The interrogation beams useful in the present invention can be of narrow or broad bandwidths and energy spectra. Moreover, the beams can be focused, collimated or divergent, as well as continuous or pulsed, depending upon the application. As used herein the term "emitted radiation" is intended to encompass gamma rays, photons and high energy particles either induced by the interrogation beam or caused by the scattering thereof. Thus, according to one embodiment of the invention, a coded aperture imaging system can utilize X-rays scattered by the object to image the object.

The invention will next be described in connection with certain illustrated embodiments. Although, the illustrations that follow are directed to the application of contraband detection, it should be clear that the invention can be applied to various other remote inspection applications, including, for example, assaying of ore during mining operations, elemental analysis during metallurgy (e.g., steel making) and monitoring manufacturing processes, generally, when the homogeneity or composition of a material must be monitored. Any material having a characteristic radiation signature (e.g. resulting from characteristic relative densities of elements) as a result of inelastic scattering of fast neutrons, can be identified using the apparatus and methods described herein. Moreover, while the systems are largely described in terms of two dimensional coded aperture and detector arrays, the same principles can be applied to construct one-dimensional systems.

BRIEF DESCRIPTION OF THE DRAWINGS

FIG. 5A illustrates the energy spectrum of carbon; FIG. 5B illustrates the energy spectrum of oxygen; and FIG. 5C illustrates the energy spectrum of nitrogen;

DETAILED DESCRIPTION

Figure 1:
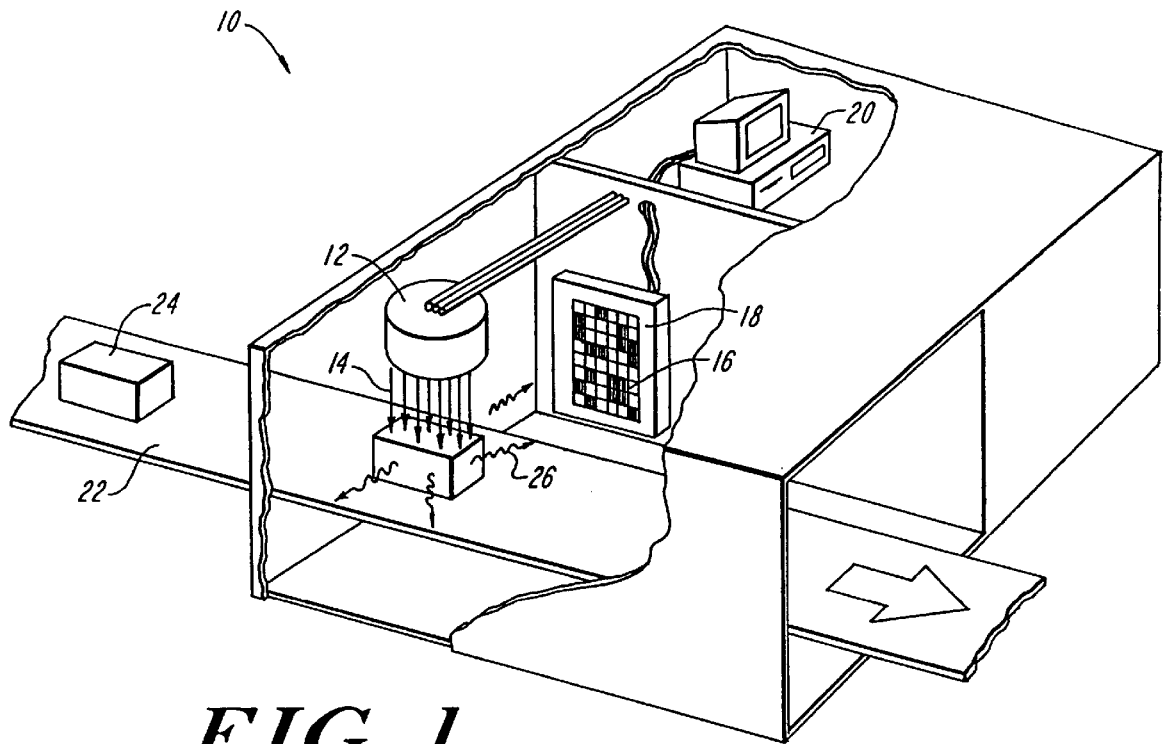
FIG. 1 is a schematic illustration of a coded aperture detection system according to the invention.

In FIG. 1, a system 10 for imaging an object according to the invention is shown including excitation source 12 which generates an energy beam 14, coded aperture 16 having a predetermined configuration, detector 18 and data processor 20. In use, a conveyance means 22 delivers a target object 24 to a location where it is interrogated by energy beam 14. The energy beam 14 causes nuclear excitation of the target object 24. In response, the nuclei of the target object 24 emit characteristic radiation. Detector 18 detects the characteristic radiation after the radiation passes through coded aperture 16 and produces detection signals representative of the energy of the detected radiation. Processor 20 characterizes target object 24 based upon the detection signals from detector 18 and based upon the predetermined configuration of coded aperture 16.

In one preferred embodiment, the nuclear excitation energy source 12 is a beam of fast neutrons. Various neutron sources can be used in the present invention including "sealed tube D-T generators" available from commercial source such as MF Physics, Inc. of Colorado Springs, Colo., or Sodern SA of Paris, France. Alternatively, linear electron accelerators with tungsten-beryllium targets, or radio frequency quadrupole linear accelerators or electrostatic accelerators can also serve as neutron sources. The sources are preferably used in conjunction with reflectors and/or collimators that direct the neutrons into a compact beam for interrogation of the object.

Fast neutrons, those with energies above about 1 MeV, are capable of penetrating materials to a depth sufficient for the examination of large objects such as luggage or cargo containers. One embodiment of this invention detects those gamma rays which are produced by neutron activation of the nuclei of elements that make up the target object. The energy of an individual emitted gamma ray is determined by which nucleus emits the gamma-ray. Thus, measuring the energy and origin point of gamma rays emitted by a target object provides the information necessary to determine the elemental composition of the target object.

Figure 2:
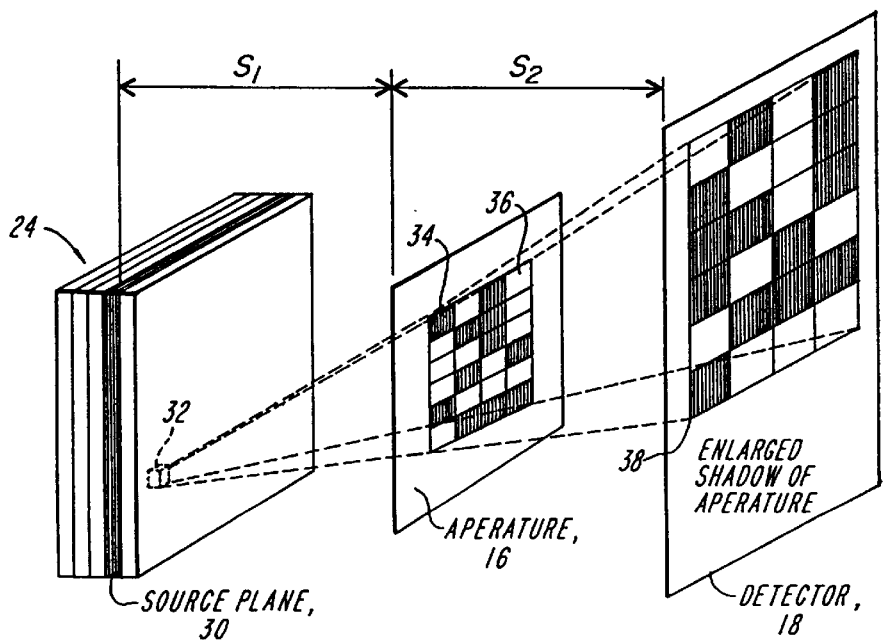
FIG. 2 is a more detailed schematic illustration showing the operation of the coded aperture and detector array of FIG. 1.

When the invention is used in the context of contraband detection by means of fast neutron bombardment, the probing neutrons interact with the contents of the object 24 and induce the material to emit gamma-rays 26. With reference to FIG. 2, the detector 18 is further illustrated in selected proximity to the target object 24 and the coded aperture 16 is disposed substantially between the target object 24 and the detector 18. Thus, gamma rays 26 emitted by a target nuclei within a particular defined volume (or "voxel") 32 are selectively passed through the coded aperture 16 and impinge on the detector 18. The coded aperture comprises aperture regions 34 and opaque regions 36. The emitted gamma-rays 26 pass through the aperture regions 34 of the coded aperture 16 and are blocked by the opaque regions 36.

As further illustrated in FIG. 2, each individual voxel 32 acts as a point source for emissions and casts a shadow of the coded aperture pattern on the detector plane. If an extensive source is used, which can be treated as multiple point sources, the multiple point sources will each cast a particular shadow of the coded aperture pattern on the detector plane, superimposing many individual patterns on the detector plane. Thus, the detector-coded aperture system operates in multiplex fashion. The detector 18 provides detection signals representative of the energy and pattern of the emitted gamma-rays. A processor 20 can subsequently characterize the target object 24 based on the detection signals.

The total number of photons (signal) recorded will be larger than that in a single pinhole system or a multihole collimator system because the total photon transmission area is increased, with every emission source contributing to many detector units. Collimators are not necessary, thus resulting in an improved signal to noise ratio (SNR). A three dimensional image can be reconstructed after decoding (de-multiplexing) the recorded signal.

With reference again to FIG. 1, a position-sensitive detector array is preferably used to record the transmitted emission signals. If detection time is not an issue, which means a long detection time is acceptable, and the photon source is stable (not time-variable), a single detector can be used to record the spatial distribution of the transmitted signal by moving through the whole shadow-casting area within a plane. Alternatively, a line detector or a two dimensional detector array can also be used. The discussion that follows focuses on one-dimensional and preferably two dimensional detector arrays in this invention because a short detection time is typically needed in practical detection applications.

Various assemblies can be used as detectors. One typical arrangement is to employ a scintillating material in conjunction with photomultipliers. Useful scintillators include sodium iodide, cesium iodide, gadolinium oxyorthosilicate (GSO), bismuth germanate (BSO), and lutethium oxyorthosilicate (LSO). The scintillators can be constructed as discrete elements or as a single large crystalline sheet. An array of photomultipliers is typically used in conjunction with the scintillator material to accurately record each incident gamma ray, its energy, and its position. Other detectors could include noble gas ionization chambers or solid state materials such as high purity germanium.

Figure 3:
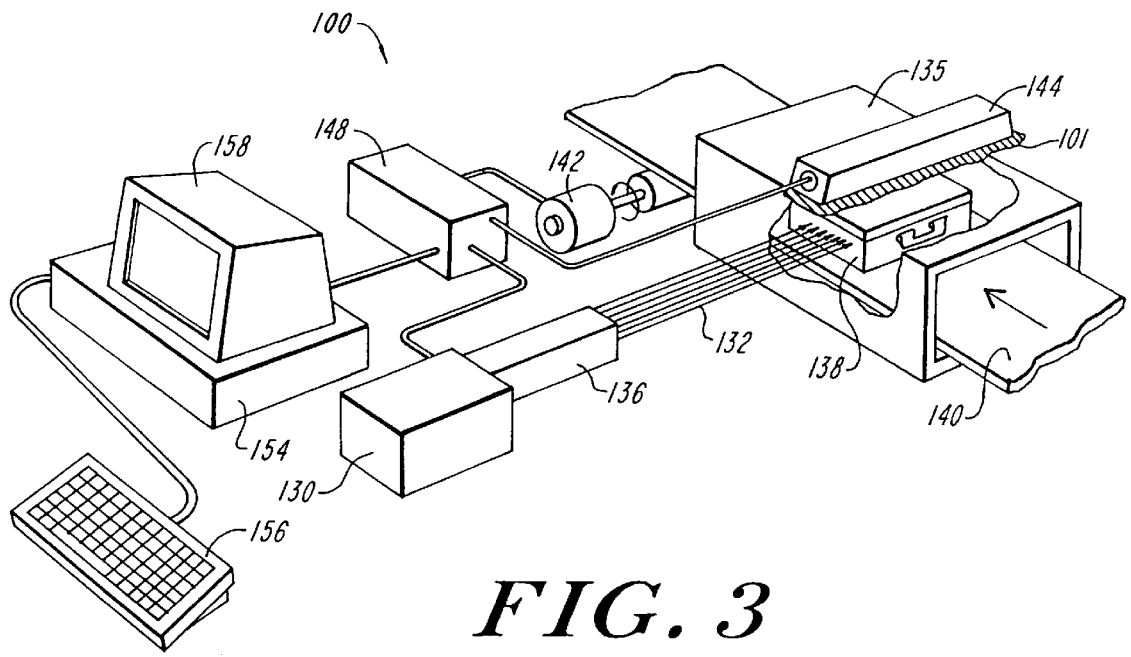
FIG. 3 is a schematic illustration of another embodiment of the present invention.

FIG. 3 illustrates an alternative embodiment 100 of the invention in which an excitation energy source (e.g., a source of fast neutrons) 130 directs an interrogation beam 132 towards an object 138, the contents of which are to be investigated. The object 138 is carried past the beam 132 within a shielded chamber 135 on a conveyor belt 140, or equivalent parcel-carrying mechanism. The conveyor belt can be driven by a motor 142 in a continuous or step-wise fashion. A detector array 144 of gamma-ray detectors is selectively positioned next to the object 134 as it is irradiated by the interrogation beam 132 within the shielded chamber 135. Appropriate control circuits 148 interface with the above-described components. The control circuits, in turn, are monitored or driven by a suitable computer 154. The computer 154 includes conventional input/output devices such as a keyboard 156, a terminal display screen 158, and/or a printer (not shown). Additional devices 160, such as non-volatile memory (e.g. disk or tape memory) may also be coupled to the computer 154, as required, in order to facilitate operation of the system to collect and/or retrieve or track the historical data that may be needed to assure a fast and reliable system performance relative to detection of various materials. The detector array and coded aperture of FIG. 3 can be a one-dimensional system operated in a scanning mode to yield three-dimensional data.

Certain elements of interest such as hydrogen (H), carbon (C), Oxygen (O), and Nitrogen (N) show up in the energy spectrum as peaks (lines of interest) at particular positions in the measured spectrum. By using appropriate processing circuits, the presence or absence of such energy peaks is monitored using a computer. If prescribed signatures of certain elements are found to be present within at least one particular small subsection of object volume, or "voxel", (see FIG. 2), of the object 24, such finding can suggest that explosives are present in that voxel of the object. Thus, the imaging capability provided by the coded aperture (described further below) combined with the signature gamma ray detection ability of the detector array provide the computer with ability to detect and localize explosive material. When such material is detected an alarm can alert operating personnel that explosive material or other contraband may be present within the object.

Figure 4:
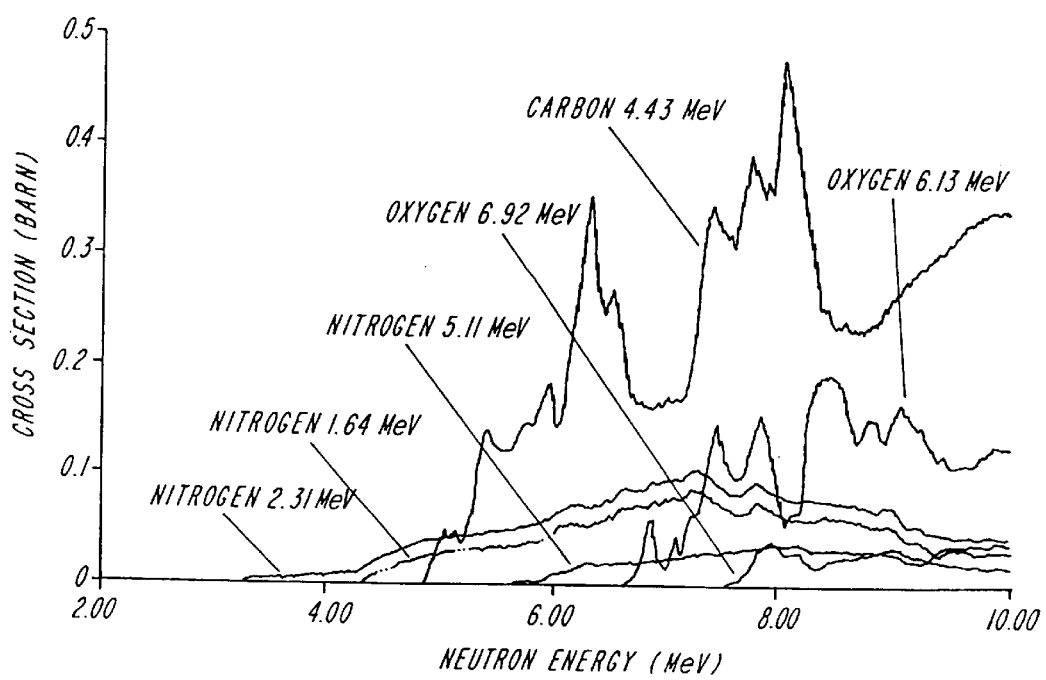
FIG. 4 is a graph of fast neutron activation cross-sections versus neutron energy for various nuclear elements.

FIG. 4 shows fast neutron activation cross-sections for various elements of interest. FIG. 4 shows the cross section (in barns) of certain atomic nuclei for the production of the indicated gamma-ray lines as a function of incident neutron energy (in MeV). The concept of nuclear cross sections is well understood by those skilled in the art and is fully disclosed in the literature.

To illustrate the manner in which the information presented in FIG. 4 is to be read, a basic understanding of the manner in which nuclear interactions occur and the corresponding measurements are made is helpful. The relevant literature fully documents such interactions and measurement techniques, see e.g. Knoll, G. F., *Radiation Detection and Measurement*, John Wiley & Sons (1979). When a neutron enters a given material, e.g. nitrogen, it has some probability to collide with an atomic nucleus so as to produce a gamma-ray. This probability is proportional to the fast neutron activation cross-section, examples of which are shown in FIG. 4. A gamma-ray is emitted only when a given amount of energy is transferred to the target nucleus. The probability that an interaction will occur, and hence the probability that a gamma-ray will be emitted significantly increases with the fluency of neutrons.

Figure 5A:
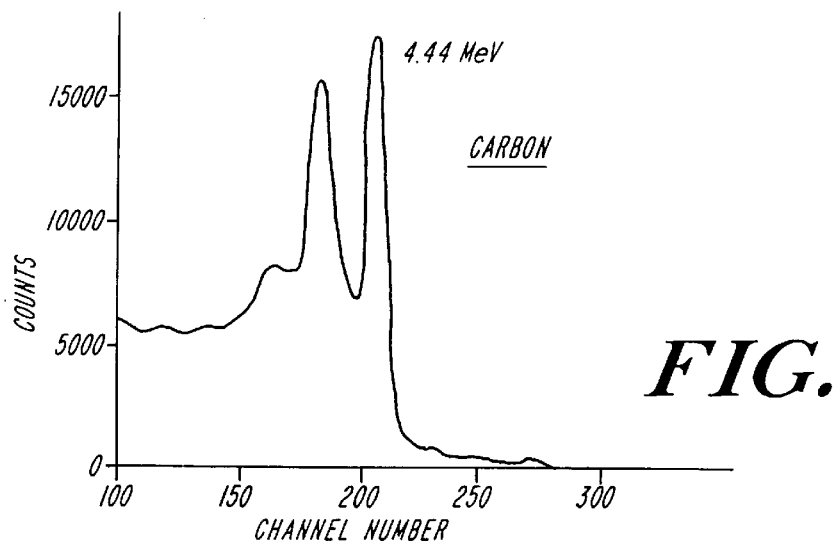
FIGS. 5A–5C are illustrative energy spectra obtained from various materials that have been irradiated with a beam of fast neutrons.
Figure 5B:
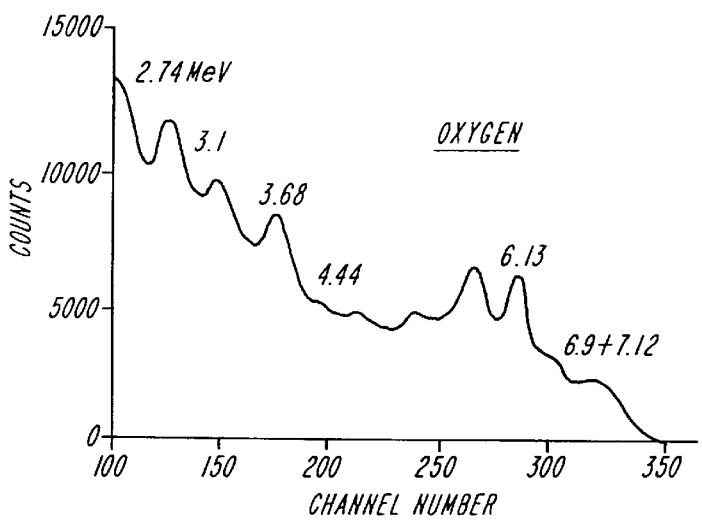
Figure 5C:
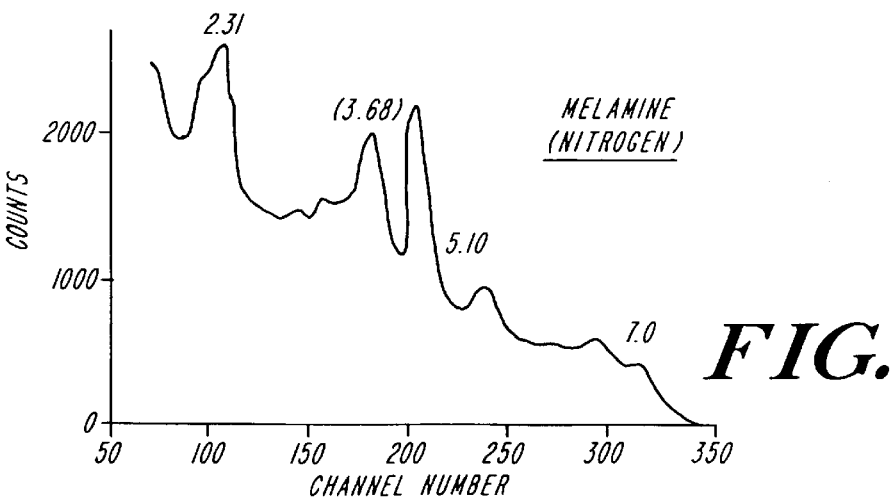

Appropriate detectors can be positioned to absorb the gamma-rays and to measure their energy. FIGS. 5A–5C show actual gamma-ray spectra measured, using realistic (non-ideal) measuring equipment and conditions, when various samples, many of which contained combinations of hydrogen, nitrogen, carbon, and/or oxygen, were irradiated with fast neutrons. Note that the vertical axis of the spectra shown in FIGS. 5A–5C is measured in "counts" where one count indicates the detection of a pulse (due to a gamma ray interaction in a scintillator detector) of the particular energy indicated by channel number on the horizontal axis. These figures are useful to show the versatility of the present invention in being able to identify the "signatures" of different types of contraband. Here, a signature of a material comprises the energy versus counts spectrum expected to be emitted by the material when irradiated by fast neutrons. These figures also illustrate the difficulty in recognizing a specified signature due to background or instrumental noise that appears in the spectrum.

The most prominent gamma peaks corresponding to neutron reactions with hydrogen, carbon, nitrogen, and oxygen are 2.225, 4.43, 2.31/5.10, 3.68/6.13 MeV, respectively.

In one embodiment according to the invention, a pulsed neutron source, such as a pulsed sealed tube source, is used. Thus, according to this embodiment, the coded aperture imaging system of the present invention can detect radiation 1) when the source is on and the nuclei are being excited by the source and 2) when the source is off. The data processor can then subtract the radiation detected when the source was off, i.e. the background radiation, from the radiation detected when the source was on. This method improves the signal-to-noise ratio.

Thus, the present invention is in part based on the phenomenon that bombardment of target nuclei by fast neutrons induces signature gamma-ray emission. The energy of the emitted signature gamma-rays reflects the elemental character of the emitting nuclei. Advantageously, the neutron activation cross sections are reasonably large.

The above description, presented in connection with FIGS. 1–5, is greatly simplified. Nonetheless, it illustrates to those less familiar with gamma-ray spectroscopy, the manner in which the present invention non-invasively detects a specified type of material, such as explosives, within a closed object.

However, the manner in which coded apertures provide spatial resolution of the sources of the gamma rays requires further description. The concept of coded aperture imaging is partly based on that of a single pinhole camera. In one example of a pinhole camera system, a sheet with a single pinhole is placed between a detector array and a source. Thus, when an individual detector in the detector array detects a photon, a processor can determine from which direction the photon came based on the location of the pinhole with respect to the individual detector.

Although the detector system can be very efficient for photons, the pinhole system severely limits the number of photons that can arrive at the detector system. The pinhole size is proportional to the sensitivity, and inversely proportional to the spatial resolution of the system. Thus, a pinhole system is of limited use for contraband detection.

A multihole collimator system consists of multiple parallel tube-like collimators and a detector system that is position-sensitive. Compared to a single pinhole system, the multihole collimator system loses tomographic (essentially depth perception) capability. Good radiography can be done; and the spatial resolution is usually higher than that of a single pinhole system. As with pinhole collimators, multihole collimators typically pass only 0.01% of the radiation emitted by the object, thus causing a substantial signal loss and possibly poor statistics for processing of the detected signals.

In the pinhole and multihole collimator systems, there is an inevitable trade-off between efficient use of (or sensitivity to) radiation emitted by the target object and spatial resolution of the emitting sources. Furthermore, Manufacturers consider other features, such as tomographic capability for a planar imaging system, in choosing a system design. In a multihole collimator system, if the detection time and the detector system are fixed, the only way to increase the sensitivity of the system to radiation emitted by a target object is to enlarge the aperture size of the collimators, which will degrade the system spatial resolution.

One solution to the trade-off between sensitivity and resolution is provided by coded aperture imaging systems. The concept behind these systems is that if one carefully chooses how to degrade the resolution of the detector system, it is possible to postprocess the detected signals to recover spatial resolution and still enjoy improved statistical quality in the processed signals. The coded aperture method uses multiple specially arranged apertures to enlarge the total (photon) transmission area without losing spatial resolution.

Coded aperture techniques are different from conventional planar imaging methods in that the detected signal is not a directly recognizable image. The signal is encoded and must be decoded before a visible image can be obtained. This is like tomography, which needs postprocessing to present the image.

Coded aperture methods include two processes: coding and decoding. First, information about the object being imaged is coded in the detected signal; second, the detected signal is decoded to form the three-dimensional (3-D) image of the object. The coding process allows the reconstruction of an object slice at a particular depth in the object while blurring other slices in the object, thus resulting in tomographic capability. The decoding process is necessary and is not an image enhancement technique, although image enhancement techniques can also be used.

Coding methods include one-dimensional (1-D) and two-dimensional (2-D) coding. A one-dimensional coding pattern is a line of specially arranged apertures, while a two-dimensional pattern is the result of a two-dimensional aperture array. The former is a special case of the latter. Various coding patterns can be employed, including the patterns of a random array, a Fresnel zone plate, and a uniformly redundant array (URA). Theoretically, the apertures can be in any shape for the same system performance, such as polygons, circles, rings, or a mixture of them. Typically, the aperture shape is the same as the cross-sectional shape of the detector unit to improve the detection efficiency.

URA patterns have been shown to have the smallest artifacts in the reconstructed images and allow detector usage ratios of 100%. In order to obtain a satisfactory image, high sensitivity and high spatial resolution are desirable. The flat side-lobes of a URA system response function make URA coding a good candidate for practical applications. The advantages of URA coded aperture methods are an improved SNR, the same resolution as that of a single pinhole imaging system whose pinhole size is the same as the aperture size in the URA pattern, minimal side-lobes of the system response function, and tomographic capability.

A uniformly redundant array coded aperture pattern for use in the present invention is preferably composed of several mosaics of a basic pattern that is pseudo-random. If the repetition time of the basic pattern in each dimension is n, it is usually required that n is at least 2. If n is larger, the system field-of-view (FOV) is larger. However, the system resolution and sensitivity are the same for $n \geq 2$ if the detectors are the same. It is necessary for n to be at least 2 to avoid the consideration of the edge effects of the coded aperture plane, and achieve a 100% detector usage ratio. It is always the case that the shadow-casting of the URA coded aperture pattern covers the area of the whole detector array. That is to say, the detectors are always within the "shadow" of the URA pattern if the object is within the system FOV. Without considering the edge effects, it can be shown that the system response function or system point-spread function (SPSF) always has flat side-lobes for large basic coded aperture patterns. If the basic pattern has enough pseudo-random units, for example, more than 41×43 apertures, it can be shown that the SPSF in the space domain is very flat except for its central peak.

URA coding methods employ a pseudo-random array as a basic pattern then repeat the basic pattern in all dimensions. The coding process is a shadow-casting operation. Radiation from a target object is encoded as it passes through a coded aperture. A detector array detects the encoded radiation and provides detection signals representative of the encoded radiation. A processor must decode the detection signals before a visible image can be obtained.

Decoding of the recorded signal can be performed as a correlation or deconvolution operation in the space domain, or a Fourier transform and filtering (multiplication) operation in the reciprocal (frequency) domain followed by an inverse Fourier transform , as described later. Other transforms, such as a Hadamard transform, can be used instead of the Fourier transform. The system point-spread function has a sharp central peak, which has the same resolution as that of a pinhole camera with the same pinhole size, but has a larger magnitude or SNR, and possibly has small side-lobe peaks which become smaller with a larger basic coding patterns. If URA coding with a large basic pattern is used, it can be shown that the SPSF is a good impulse function δ(x, y) in the space domain.

Coded aperture imaging methods have tomographic capability. Only one slice is decoded each time. For a different slice, the decoding function (matrix) is different by a scaling factor. Multiple such decoded slices together form the whole 3-D reconstructed image. The following discussion is based on the decoding of a single slice; and the variable z is used to indicate the depth coordinate of the slice.

A reconstructed image is obtained by $$R(x, y, z)=S(x, y, z) \oplus H(x, y, z),$$

where z is the coordinate of the axis that is perpendicular to the coded aperture plane, x and y are the coordinates of the axes such that the x, y, and z axes form a Cartesian coordinate system, S(x, y, z) is the source distribution function, H(x, y, z) is the system point-spread function or system (pulse) response function, R(x, y, z) is the reconstructed image function, and $\oplus$ denotes a convolution operation.

In actual applications, the imaging steps are as follows:

Record all signals from the sources that are imaged;

Fix z and reconstruct the corresponding slice of the object;

Change z and repeat the previous step to reconstruct other slices of the object;

Combine all reconstructed slices to obtain the final 3-D image of the object under examination.

There are several methods for decoding which include but are not limited to deconvolution, correlation, Fourier transform, and Hadamard transform methods. In the following description, 2-D coding and decoding are assumed, of which 1-D coding and decoding are just a special case.

A deconvolution is the reverse operation of a convolution. Assume A and B are two m×r matrices; $a_{i,j}$ and $b_{i,j}$ are their elements respectively. Their convolution matrix C is defined as $$C(x, y)=A(x, y) \oplus B(x, y),$$

with each element of C as $$C_{x,y} = \sum_{i=o}^{m} \sum_{j=0}^{n} a_{i,j} b_{(x-i),(y-j)},$$

where matrices A and B are filled with zero outside the m×n dimension. The reverse operation is called deconvolution. However, a precise deconvolution is not always possible. An approximation of the deconvolution operation ($\oplus^{-1}$) is $$B(x, y)=C(x, y)\oplus^{-1}A(x, y)+E(x, y),$$

where E is a noise or error matrix. If C=A⊕B, then E=O, and this is a precise deconvolution operation. Generally, E≠O, however, the noise matrix E can be omitted for simplicity. In such an instance, C=A⊕B is just an approximation of the deconvolution operation, and may cause side-peaks in the SPSF and distortion (artifacts) in the reconstructed images.

A correlation (Θ) of two matrices is defined as $$C(x, y)=A(x, y) \Theta B(x, y),$$

with each element of matrix C as $$C_{x,y} = \sum_{i=o}^{m} \sum_{j=0}^{n} a_{i,j} b_{(i-x),(j-y)},$$

where A and B are two m×n matrices with their elements outside the m×n dimension filled with zero, $a_{i,j}$ and $b_{i,j}$ are their elements respectively, C is their correlation matrix, $c_{x,y}$ is its element, and Θ denotes a correlation operation. If A and B are identical, then C is called the autocorrelation of matrix A (or B). A correlation shows the degree of relation of two matrices; thus, an autocorrelation matrix usually has a strong central peak. Typically, the larger the dimension of a matrix, the sharper the central peak of the autocorrelation matrix. However, the distribution and values of the matrix elements also affect the shape and magnitude of the central peak.

A normal (positive) decoding algorithm uses the coding matrix itself as the decoding matrix; thus the SPSF is the autocorrelation operation of the coding matrix, and this is called a matched normal (positive) decoding algorithm. A good coding matrix design produces an autocorrelation matrix with a sharp central peak and flat side-lobes; such a coding matrix design results in a large SNR and a narrow full-width-half-magnitude (FWHM) value of the central peak of the SPSF. In other words, such a coding matrix design produces an coded aperture imaging system with high sensitivity and high spatial resolution.

A subtraction decoding algorithm uses negative values for some elements in the decoding matrix and decreases the magnitude of the side-lobes of the SPSF. For example, if the coding matrix consists of 0 and 1, the decoding matrix (called the G function) can use −1 and 1, respectively, and this is called the matched subtraction decoding algorithm. Another example is that the decoding matrix G uses $$\frac{m}{m-n}$$

and 1, respectively, and is called the balanced decoding algorithm because the side-lobes of the SPSF are "balanced" or smaller. Thus, the SPSF is more like a δ function in the space domain.

Decoding can be done by using Fourier transform methods with filtering, in either the reciprocal (frequency) domain, or the space domain. A convolution operation in the space domain is equivalent to a multiplication operation in the reciprocal (frequency) domain, $$A \oplus B = \Im^{-1}\{\Im\{A\} * \Im\{B\}\};$$

while the relation of a cross-correlation operation in the space domain with its counterpart in the reciprocal (frequency) domain is $$A \Theta B = \Im^{-1}\{\Im\{A\}^* * \Im\{B\}\},$$

where * means a conjugate, * means a multiplication operation of two matrices and is "single-element-to-element," rather than a normal matrix multiplication operation, $\Im$ denotes a Fourier transform operation, $\Im^{-1}$ denotes an inverse Fourier transform operation, and A and B are matrices in the space domain. The operation, e.g. convolution, performs the decoding or filtering, and the decoding function or the filter is a matrix. The correlation decoding methods described previously can also be implemented by Fourier transform methods.

One expects the SPSF is a δ function in the space domain, which means it is uniform in the reciprocal (frequency) domain, thus causing no distortion for any frequency. This is the case when a large basic URA coding pattern is used. However, if the basic URA pattern is not very large, a filter matrix can be used to improve the system performance and make the SPSF as $$\Im\{H\}=\Im\{C\}*\Im\{G\}=I,$$

where I is a matrix in which all diagonal elements are 1, C is the coding matrix, G is the filter or decoding matrix, and H is the SPSF matrix. H, C, and G are in the space domain. If $c_{i,j}$, $g_{i,j}$ and $h_{i,j}$ are the ith row and jth column elements of the matrices $\Im\{C\}, \Im\{G\}$, and $\Im\{H\}$ respectively, then $$h_{i,j}=c_{i,j}\times g_{i,j}$$

where × denotes a normal multiplication operation of real or complex numbers. Because $$h_{i,j}\equiv 1,$$

one obtains $$g_{i,j} = \frac{1}{c_{i,j}}$$

If $c_{i,j}=0$, one may set $g_{i,j}$ as a very large constant number instead of infinity. It makes the SPSF a δ function or nearly a δ function in the space domain. Hence, the system has high spatial resolution with minimal distortion.

Decoding can be implemented in the space domain. After obtaining a Fourier transform of the coding matrix, based on the filter matrix design discussed above, one can obtain the Fourier transform of the SPSF (a FTSPSF). Taking an inverse Fourier transform of the FTSPSF gives the system (pulse) response function SPSF in the space domain. Practically, one can take an inverse Fourier transform of $\Im\{G\}$ to get the decoding function (matrix) in the space domain; then the convolution of the matrix of the signal detected with the decoding matrix in the space domain yields the reconstructed image slice, which is $$R(x, y, z)=D(x, y)\oplus G(x, y, z),$$

where D is the matrix of the detected signal, z is the coordinate of the image slice that is decoded, G is the decoding function (matrix), and R is the matrix of the decoded image slice. R, D, and G are matrices in the space domain.

Decoding can be implemented in the reciprocal domain, i.e. the frequency domain. Based on the filter design discussed above, one can take a Fourier transform of the matrix of the detected signal and multiply it with $\Im\{G\}$, then one can take an inverse Fourier transform to obtain the reconstructed image as follows:

$$R(x, y, z)=\Im^{-1}\{\Im\{D(x, y)\}*\Im\{G(x, y, z)\}\},$$

where R is the matrix of the decoded (reconstructed) image slice (corresponding to coordinate z), $\Im\{D(x, y)\}$ is the matrix of the detected signal, and $\Im\{G(x, y, z,)\}$ is the matrix of the decoding function (for the image slice corresponding to coordinate z). R is in the space domain while the other matrices are in the reciprocal (frequency) domain. The variable z corresponds to the slice being decoded. Similar expressions for the correlation decoding methods in the space domain can also be obtained.

Hadamard Transform Methods can also be used. These methods are similar to the Fourier transform methods, except that they are convenient for correlation operations in the space domain if the matrix elements have only two values such as 1 and −1.

In general, convolution with the coding function itself should not be used as the SPSF because the SPSF is typically poor in that case, no matter whether a (matched) positive or subtraction decoding algorithm is used. A deconvolution is complex and can produce residues which cause noise; thus, it is not recommended. The correlation and Fourier transform methods are two good ways for implementing decoding in coded aperture imaging methods. For small basic URA patterns, the correlation method is simpler and preferable; while for large basic URA patterns, the Fourier transform method is faster and preferable.

For a URA coded aperture plane with a basic pattern composed of (2s −1) by (2s+1) aperture units, where s is a positive integer, it can be shown that the SPSF using a correlation decoding method (the basic pattern correlates with the whole URA pattern) has very flat side-lobes. Hadamard transforms In so produce very flat side-lobes.

In one embodiment according to the invention, an extended Hadamard cyclic difference set coded aperture is used. A cyclic difference set can be defined such that the rotated versions of the set have the same property as the original set. A Hadamard array can be composed of elements equal to 0 or 1, and its rows and columns are mutually orthogonal. An extended Hadamard array can be an array composed of elements equal to 0 or 1. Thus an extended Hadamard cyclic difference set can be an array composed of elements equal to 0 and 1, and all of the rotated versions of the array including the original array each have the same "inner product" value. In other words, all of the rotated versions of the array including the original array have the same peak value for the elements of their respective cross-correlation matrices. A Hadamard set represents pinhole sets. Thus, one embodiment of the invention uses extended Hadamard cyclic difference sets to include all circulates or cyclic difference sets which are composed of elements equal to 0 or 1.

The spatial resolution of the imaging system of this invention is determined by the object-imaging system geometry. In neutron activation analysis techniques, there exists a need to lower the dose to the object under examination, and to collect high energy gamma rays. For these reasons, in one embodiment, the invention uses high density large geometry scintillation detectors to detect, in a short time, a sufficient number of photons for imaging. In one embodiment, 10×10× 10 cm³ sodium iodide (NaI) detectors are used.

In one embodiment of this invention, photon energies from 1 MeV to 6.13 MeV are of interest. As a result of the high energy of the photons, the coded aperture is more "transparent" in the opaque regions. High energy photons and short-distance sources make this implementation of a coded aperture imaging system different from other implementations. In addition, one goal of the invention is "detecting" selected nuclear elements and localizing the 3-D positions of the special nuclear elements to provide elemental composition and density information. This information is used for decision making rather than for obtaining a very good (3-D nuclear elemental distribution) image; this makes the artifacts in the reconstructed image for a small URA pattern tolerable.

In order to use digital equipment such as a computer for processing, one needs to represent the data digitally. For transparent (open) apertures, the corresponding detector units are assigned 1; while for opaques, the corresponding detector units are assigned 0. This assignment assumes that no photons are attenuated in the transparent aperture area and no photons transmit the opaque area. This is not the actual case; and adjustments in simulations and actual decoding processes can be made based on the imperfect absorption and transmission of photons.

A coded aperture plane can be self-supportive or not. If it is not self-supportive, which means not all opaques are connected to each other, then a low photon attenuation supporting plane is necessary, although it decreases the SNR. A coded aperture plane should be made of high Z (atomic number) and high density materials for the best photon shielding effect. Candidate materials for such a purpose are lead (atomic number Z=82, physical density $\rho$=11.36 g/cm$^3$), sintered tungsten (atomic number Z=74, physical density $\rho$=17 g/cm$^3$), and depleted uranium ($^{238}$U) (atomic number Z=92, physical density $\rho$=18.68 g/cm$^3$).

The basic pattern in a URA design should obey the following rules:
  as large as possible,
  pseudo-random,
  (2s−1) by (2s+1) aperture units, where s is a positive integer,
  the number of aperture units in the coded aperture should be one greater than the number of opaques units.

In addition, in a URA pattern, the repetition times of its basic pattern should be at least 2 in each dimension; otherwise, the detector system must be large enough to contain the whole shadow of the coded aperture pattern, thus causing the detector usage ratio to be less than 100%.

A self-supportive pattern is preferable to avoid the requirement of a support structure. A support structure can decrease the SNR. A self-supportive pattern is a pattern where all opaque units are connected to each other, either at corners, or directly side to side or top to bottom.

URA coded aperture imaging methods have very flat sidelobes in the system response function. A random pattern should be used for each basic pattern. E. E. Fenimore in *Coded Aperture Imaging With Uniformly Redundant Arrays*, Applied Optics, 17(3):337–347, February 1978 suggested that the pseudo-noise array described by Calabro and Wolf can be used to design the basic pattern, which has (2s−1) by (2s+1) aperture units. This is true for a very large basic pattern, for example, when s is at least 21.

In an implementation of the present invention, large sodium iodide (NaI) scintillation detectors (a 10×10 cm$^2$ cross-sectional area for each detector) were used to form an 8 by 8 array; thus the dimension of the pixels was limited to 8 by 8. At this setting, a 7 by 5 coded aperture pattern is optimal. Many coded aperture designs from 8×8, 8×7, 8×6, 7×7, 7×6, and 7×5 basic patterns have been tried. Among them, 7×5 basic patterns have the best performance, which means the flattest side-lobes of the system response function.

Designs based on Fenimore's suggestions have been tried, and the SPSF results for a 7×5 basic pattern are shown in FIGS. 6C–6F. This design is not the best case because Calabro and Wolf's description of the pseudo-noise array applies to large patterns, while the basic pattern of this invention is a relatively small 7×5 array. For one embodiment of the invention, it is possible to design the basic pattern manually for optimal performance.

Theoretically, a 7 by 5 pattern has $C_{35}^{18}$ or roughly 4.5×10$^9$ different cases of design. However, choices are limited and thus manual optimization is possible after one considers the following rules to obtain a good system response function:

The transparent (open) and opaque apertures should distribute roughly evenly in space;
  The basic URA pattern should be pseudo-random;
  The basic pattern contains 18 holes (open apertures) and 17 opaques;
  The URA plane is self-supportive.

Figure 6A:
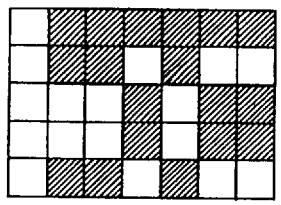
FIGS. 6A and 6B show one example of a 7×5 a uniform redundant array (URA) coded aperture pattern and a two-mosaic (in each dimension) pattern, respectively.
Figure 6B:
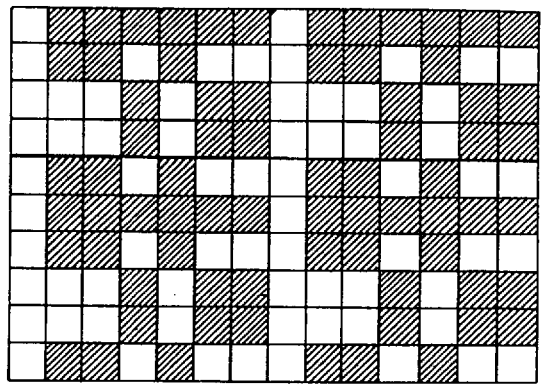
Figure 6C:
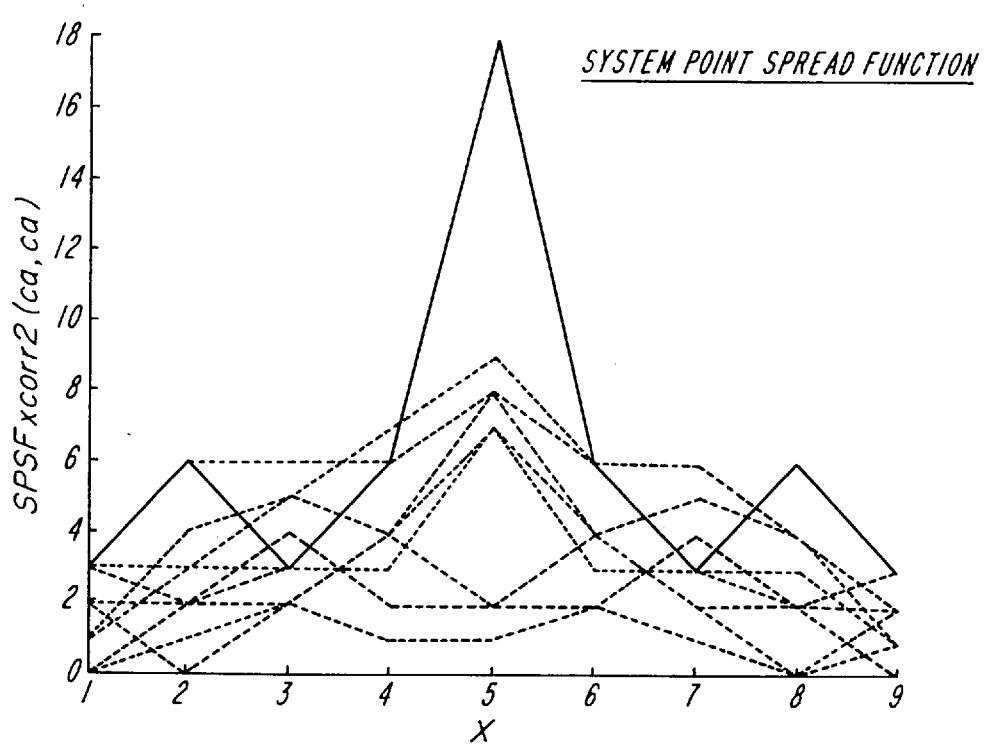
FIGS. 6C and 6E show two-dimensional system point-spread functions corresponding to the URA of 6A, based on a matched normal (positive) decoding algorithm and a matched subtraction decoding algorithm, respectively for use in the present invention.
Figure 6D:
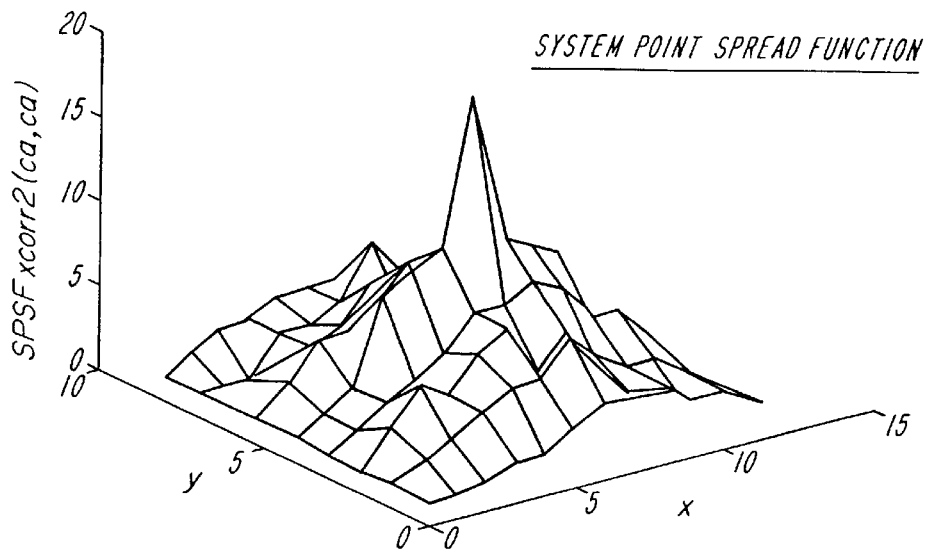
FIGS. 6D and 6F are the three-dimensional system point-spread functions of FIGS. 6C and 6E, respectively.
Figure 6E:
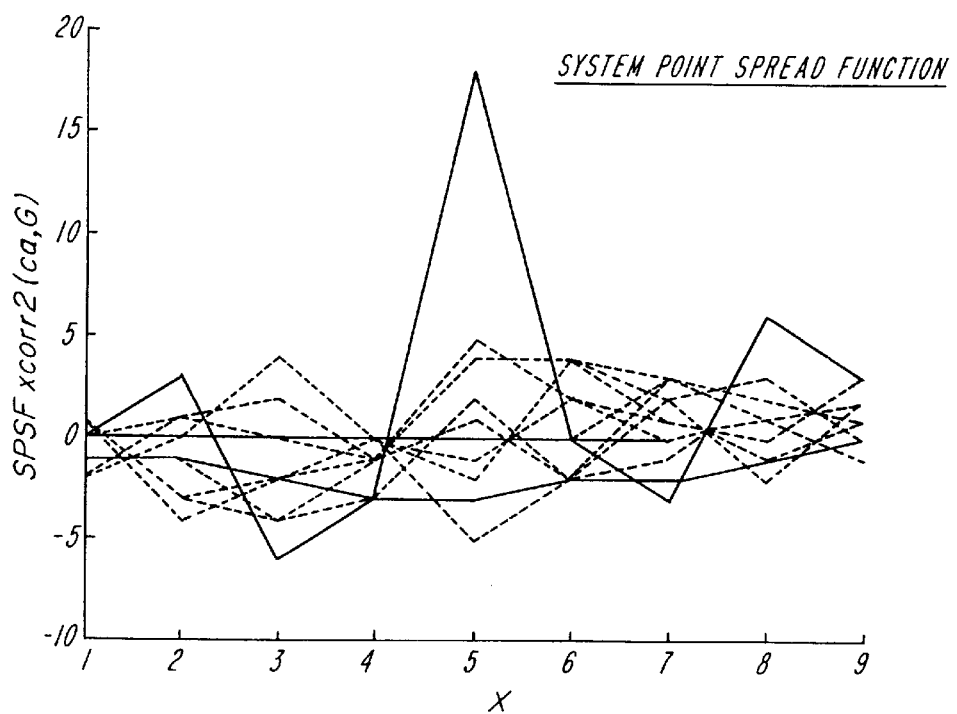
Figure 6F:
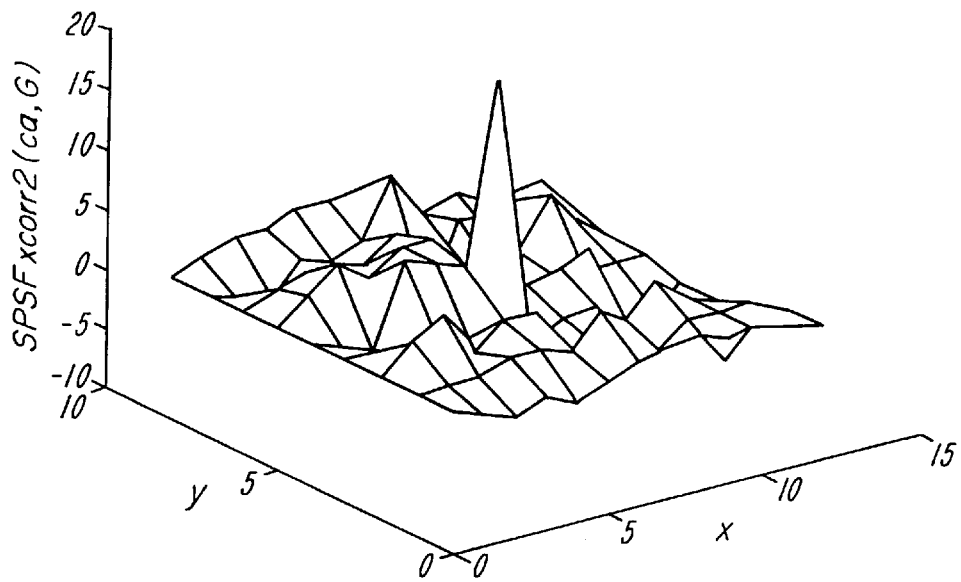

In implementing one embodiment of the invention, about 30 designs were investigated, and a preferred design is shown as a 7×5 mosaic and a two-pattern mosaic in FIGS. 6A and 6B, respectively.

FIG. 6 shows URA coded aperture design 1: a pseudo-noise pattern and its SPSF. This design is based on Fenimore using the Pseudo-Noise function of Calabro and Wolf. The basic 7×5 pattern is drawn in (a). A two-mosaic (in each dimension) pattern is drawn in (b). The SPSF based on a matched normal (positive) decoding algorithm is plotted as cross-sectional and three-dimensional views in (c) and (d) respectively. The SPSF based on a matched subtraction decoding algorithm is plotted as cross-sectional and three-dimensional views in (e) and (f) respectively. One can see that the SPSF is not as good as that shown in FIG. 7 because this pseudo-noise function should apply to large basic URA patterns.

Figure 7A:
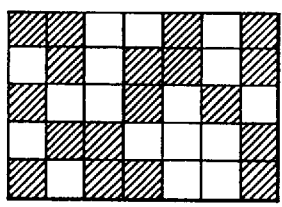
FIGS. 7A and 7B show a second example of a 7×5 URA coded aperture pattern and two-mosaic pattern, respectively.
Figure 7B:
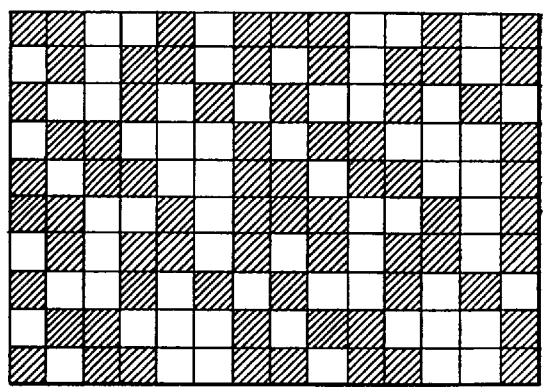
Figure 7C:
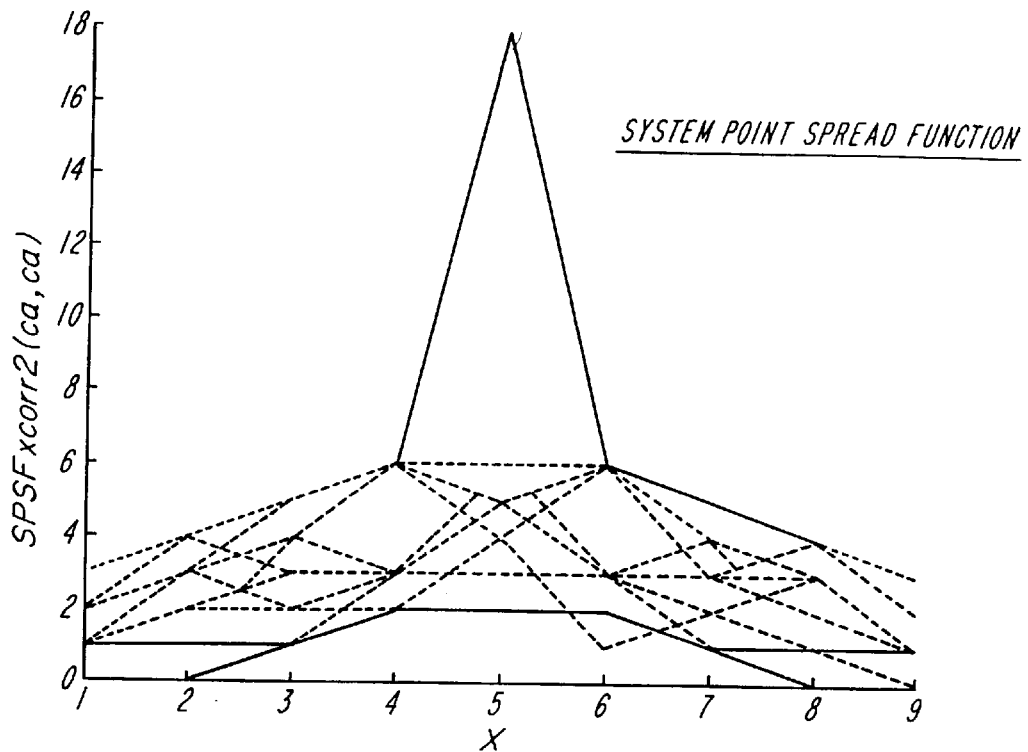
FIGS. 7C and 7E show two-dimensional system point-spread functions corresponding to the URA of FIG. 7A, based on a matched normal (positive) decoding algorithm and a matched subtraction decoding algorithm, respectively.
Figure 7D:
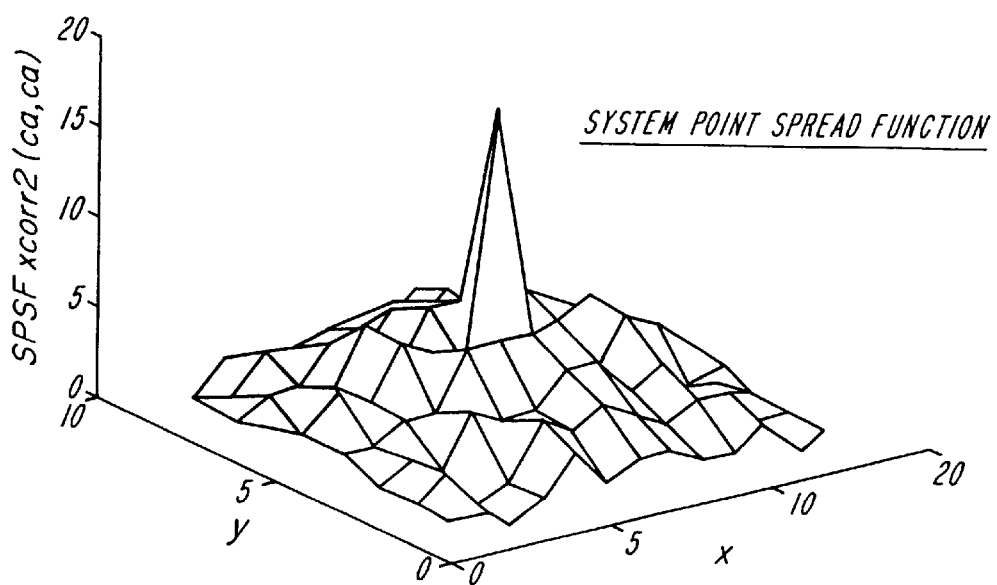
FIGS. 7D and 7F are the three-dimensional system point-spread functions of FIGS. 7C and 7E, respectively.

FIGS. 7A shows URA coded aperture design 2: a preferred pattern and its SPSF. A two-mosaic (in each dimension) pattern is drawn in (b). The SPSF based on a matched normal (positive) decoding algorithm is plotted as cross-sectional and three-dimensional views in (c) and (d) respectively. The SPSF based on a matched subtraction decoding algorithm is plotted as cross-sectional and three-dimensional views in (e) and (f) respectively. Note the flat side-lobes of the SPSF, especially when a matched normal (positive) decoding algorithm is used.

Figure 7E:
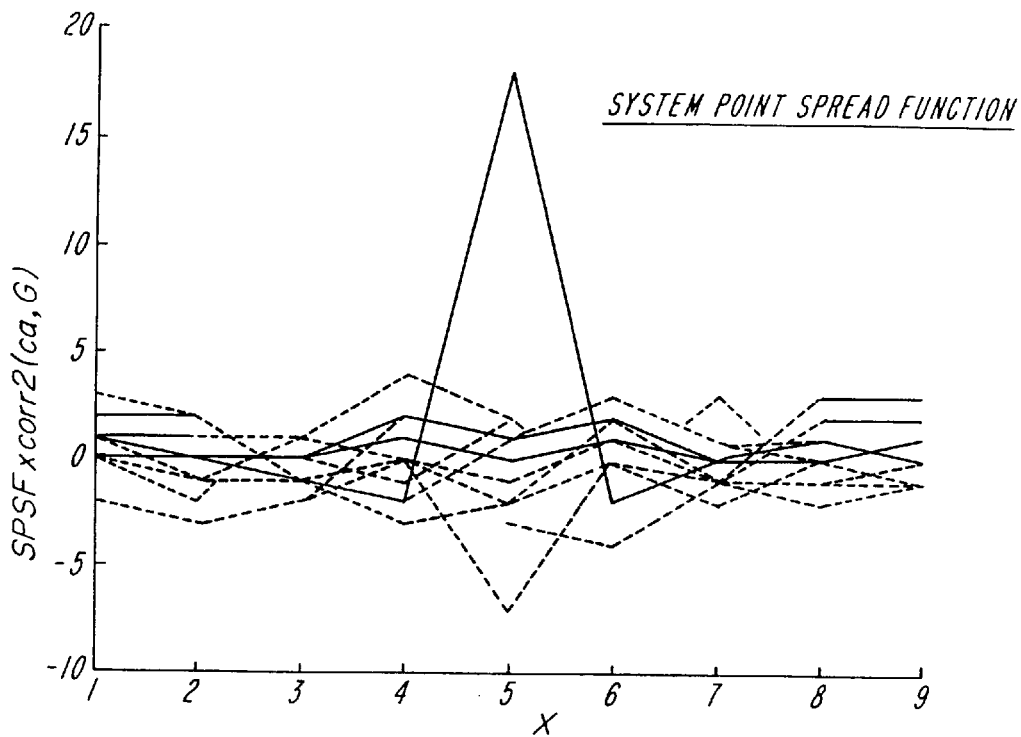
Figure 7F:
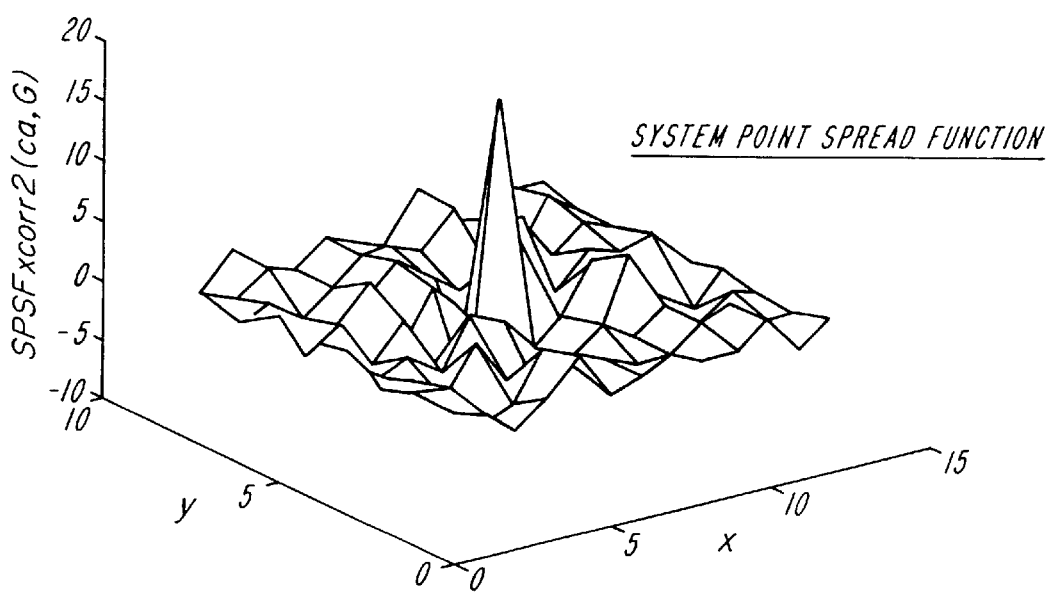
Figure 8A:
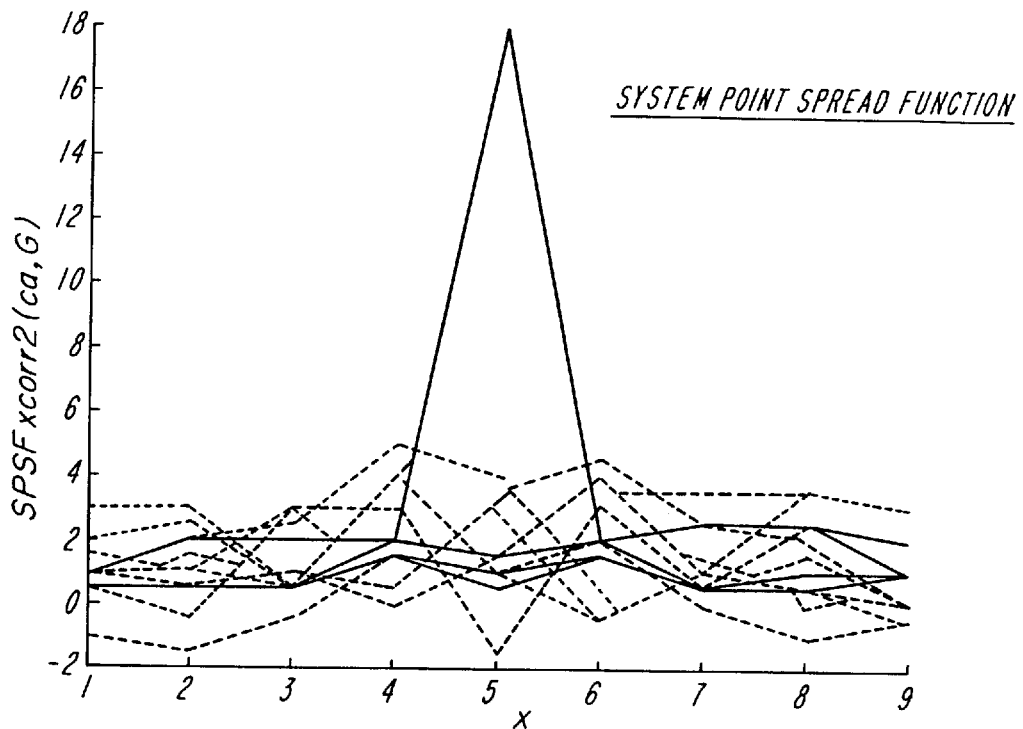
FIGS. 8A and 8B show a two and corresponding three dimensional system point-spread function, respectively for the URA pattern of FIG. 7A using a balanced decoding algorithm.

FIG. 8A shows the SPSF for URA coded aperture design 2 based on a balanced decoding algorithm. The decoding function (matrix) uses m/(m-n) instead of −1, where m is 6 and n is 18 in this design. The SPSF based on this balanced decoding algorithm is plotted as cross-sectional and three-dimensional views in (a) and (b) respectively. Note the SNR is improved over that based on the matched (but unbalanced) decoding algorithm shown in FIGS. 7E and 7F.

A matched normal (positive) decoding algorithm occurs when the decoding matrix is the coding matrix itself, and a matched subtraction decoding algorithm occurs when the decoding matrix uses −1 instead of 0. A balanced decoding algorithm occurs when the decoding matrix uses m/(m-n) instead of −1, as described below with respect to the G function. For all these algorithms, the decoding process is a correlation operation and no filters are used. Note the flat side-lobes of the SPSF in FIG. 7A where a preferred pattern design is shown, especially if a matched normal (positive) decoding algorithm is used, which corresponds to the "intrinsic" behavior of the coded aperture pattern and is the starting point of the preferred pattern design. If a filter is used as the decoding matrix, as described in the Fourier transform methods above, the SNR can be increased by making the SPSF approximately a $\delta$ function, although this is not the "intrinsic" behavior of the system and other system performance parameters could be effected. The maximum $$\sqrt{\frac{N}{2}}$$

improvement of the SNR for URA coded aperture methods is the limit for a matched normal (positive) decoding algorithm, which causes the SPSF to have the same spatial resolution as that of a corresponding single pinhole camera.

Note that for a small basic pattern, the ½ transparency rate rule still applies. However, Fenimore's suggestion of using the pseudo-noise function of Calabro and Wolf is not valid any more. This suggestion is only suitable for large basic patterns. Fortunately, for a small basic pattern, manual design is possible. Importantly, a difference in a small basic pattern design could result in a large change in the system response function because it is more difficult to design a pseudo-noise arrangement in a small pattern than in a large pattern. This difficulty indicates that carefully designed coded apertures are needed to achieve optimal performance of coded aperture imaging systems. Various simulations have been performed to analyze the designs of a 7×5 basic pattern, as well as other patterns. Fenimore has shown that a basic URA pattern with r by r−2 units has good response, where r is an odd number. The simulation results according to the present invention were consistent with Fenimore's findings.

Figure 8B:
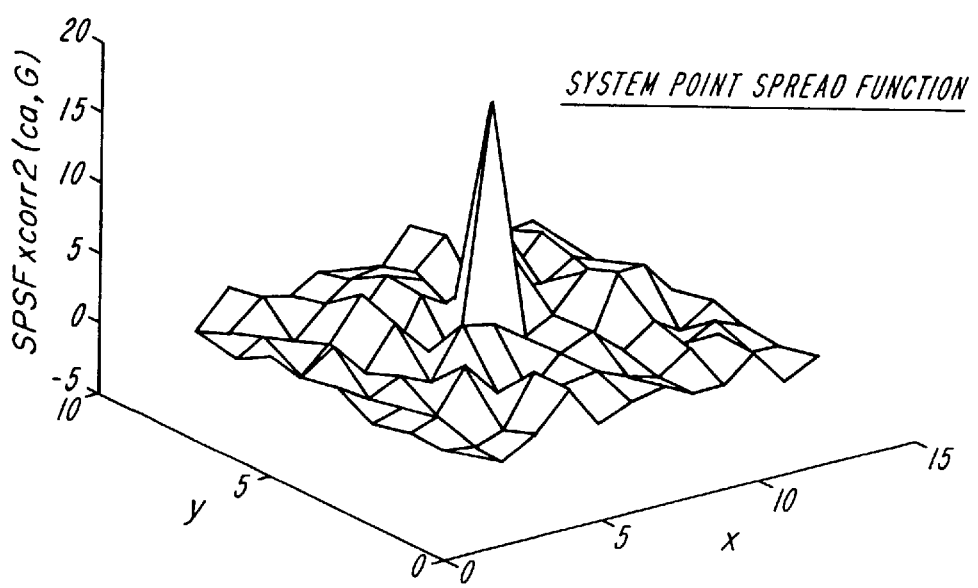

Some researchers suggest that the decoding function G should have the following features:

G(x, y)=1 (when (x, y) corresponds to a hole), m/(m-n) (when (x, y) corresponds to an opaque), where m is the value of the side-lobes of C ⊕ C, and n is the number of transparent (open) apertures. The value of m is 9 for the pseudo-noise pattern shown in FIG. 6A, and is 6 for a preferred pattern shown in FIG. 7A. A balanced decoding algorithm uses this G function (matrix), and the SPSF for the pattern of FIG. 7A is shown in FIGS. 8A and 8B, where one can see the SNR is larger than that in the matched decoding algorithm case. For the pseudo-noise pattern shown in FIG. 6A, the balanced decoding algorithm is the same as the matched decoding algorithm.

System response functions based on a matched normal decoding algorithm for a preferred design are shown in FIGS. 7E–7F. Note the matched normal (positive) decoding algorithm yields a very smooth SPSF for the design, and the SNR is 3. The coded aperture theory predicts that the maximum improvement of the SNR of a URA coded aperture imaging system with a 7×5 basic pattern over a single pinhole camera is $$SNR(\text{best}) = \sqrt{\frac{N}{2}} = 3,$$

where N is the number of open apertures, 18 in this case. The SNR is proportional to the square root of the number of photons collected because of the statistical nature of the photon detection. In addition, because the multiplexing in the coded aperture methods increases signal and noise (called the multiplexing noise) at the same time, the net increase of the SNR in a coded aperture imaging system is $$\sqrt{\frac{N}{2}},$$

where N is the increase of the number of photons collected, and is the same as the number of open apertures in a coded aperture imaging system (compared to a single pinhole camera system). If a balanced decoding algorithm is used, or a filter is used, such as that in the Fourier transform methods, the SNR will increase because the SPSF is more like a function in the space domain. However, if a filter is used, the SPSF is not the "intrinsic" response of the system.

Fast neutron activation analysis techniques combined with coded aperture imaging methods are novel in explosive and drug detection. High electron density materials should be used to make the opaque regions in the coded aperture plane so as to produce opaque regions that will not transmit photons emitted from the target object 24 to the detector 18. This invention requires high Z (atomic number) and high physical density materials. Depleted uranium ($^{238}$U) is a good candidate because it has a very high electron density and a small fast neutron reaction cross-section. However, the fabrication cost is high because of its hardness. In one embodiment, this invention uses lead as the photon shielding material supported by an aluminum plane because lead is cheap and easily available, although depleted uranium has better properties for high energy photon shielding. Alternatively, Hevimet (sintered tungsten) is another option.

Monte Carlo simulations for 1.25 MeV and 6 MeV photon sources have been carried out to test the system performance. These photon energies simulated the actual signature gamma-ray energies in explosive detection. In the simulations, coded aperture plane materials were lead and depleted uranium. Lead is easily shaped and is a normal photon-shielding material and thus easily available. Depleted uranium has a high electron density, and thus is an excellent photon-shielding material. Both materials, as well as Hevimet, are potentially usable in the coded aperture plane fabrication.

According to another embodiment, the coded aperture imaging of the invention is applied in metal processing to determine the elemental composition of molten alloy in a rapid, non-invasive manner. According to yet another embodiment, the coded aperture imaging of the invention is applied to the analysis of mineral ores to assist in subsequent processing of the ores.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense. It is also to be understood that the following claims are intended to cover all of the generic and specific features of the invention as described herein, and all statements of the scope of the invention which, as a matter of language, might be said to fall there between.

I claim:

1. An apparatus for analyzing radiation emitted by an object in response to neutron bombardment, the apparatus comprising a radiation detector array for detecting the energy of gamma rays emitted by the object in response to neutron bombardment and for producing detection signals responsive to the energy of the detected gamma rays, the neutrons having interacted with atomic nuclei of the elements contained within the object to produce gamma-rays characteristic of the elements contained within the object;

a coded aperture, having a predetermined configuration, disposed between the detector array and the object such that emitted radiation is detected by the detector array after passage through the coded aperture; and a data processor for characterizing the object by substantially determining the elemental composition of the object, the elemental composition being indicated by the location, number and energy spectra of the gamma ray sources located within the object, the location, number and energy spectra of gamma ray sources being substantially determined by the data processor based upon the detection signals produced by the detector array, and the selected configuration of the coded aperture.

2. A method of analyzing radiation emitted by an object in response to nuclear interrogation, comprising the steps of:

disposing a coded aperture, having a predetermined configuration, in selected proximity to the object;

interrogating the nuclei of the object with an energy source, the interrogation resulting in emitted radiation, said interrogating step including bombarding said object with fast neutrons, detecting, with a detector, at least a portion of the radiation emitted in response to the nuclear interrogation, the detector producing detection signals responsive to the radiation incident upon the detector after passage through the coded aperture; and processing the detection signals to characterize the object based upon the emitted radiation detected by the detector, and based upon the predetermined configuration of the coded aperture.

3. The method of claim 2, wherein the step of interrogating nuclei of the object further comprises bombarding the object with neutrons having energies from about 1 to about 15 MeV.

4. A method of analyzing radiation emitted by an object in response to nuclear interrogation, comprising the steps of:

disposing a coded aperture, having a predetermined configuration, in selected proximity to the object;

interrogating the nuclei of the object with an energy source, the interrogation resulting in emitted radiation, said interrogating step including bombarding said object with fast neutrons, detecting, with a detector, at least a portion of the radiation emitted in response to the nuclear interrogation, the detector producing detection signals responsive to the radiation incident upon the detector after passage through the coded aperture; and processing the detection signals to characterize the object based upon the emitted radiation detected by the detector, and based upon the predetermined configuration of the coded aperture, wherein said processing step comprises determining the presence of elements of interest, and determining the relative densities of elements of interest, wherein said elements of interest are selected from the group consisting of at least oxygen, carbon, nitrogen, hydrogen, and chlorine.

5. A method of analyzing the elemental composition of an object in response to neutron bombardment, comprising the steps of disposing a coded aperture having a predetermined configuration in selected proximity to the object;

generating a beam of fast neutrons;

irradiating the object with the beam of fast neutrons, the fast neutrons interacting with atomic nuclei of the elements contained within the object to produce gamma-rays characteristic of the elements contained within the object;

measuring the characteristic spectral lines of the gamma-rays using a radiation detector array and a data processor, the gamma-rays having passed through the coded aperture disposed between the object and the radiation detector array;

determining density distributions of the elements contained within the object based upon the measured characteristic spectral lines and the predetermined configuration of the coded aperture;

comparing the density distributions with known density distributions of the elements of interest.

6. The method of claim 5, wherein said irradiating step further comprises irradiating the object with a pulsed beam of neutrons.

7. The method of claim 5, wherein said elements of interest are selected from the group consisting of at least oxygen, carbon, nitrogen, hydrogen, and chlorine.

8. The method of claim 5, wherein the method of analyzing the elemental composition includes determining the proportion of any one or more metals in a compound, ore, or alloy.

9. The method of claim 8, wherein the metals include precious metals.

* * * * *